(12) United States Patent
Gramaglia

(10) Patent No.: US 11,103,376 B1
(45) Date of Patent: Aug. 31, 2021

(54) ORTHOTICS BRACE AND SYSTEM

(71) Applicant: Ernest Gramaglia, Magnolia, NJ (US)

(72) Inventor: Ernest Gramaglia, Magnolia, NJ (US)

(*) Notice: Subject to any disclaimer, the term of this patent is extended or adjusted under 35 U.S.C. 154(b) by 0 days.

(21) Appl. No.: 16/920,674

(22) Filed: Jul. 4, 2020

(51) Int. Cl.
*A61F 5/01* (2006.01)

(52) U.S. Cl.
CPC .......... *A61F 5/0127* (2013.01); *A61F 5/0113* (2013.01)

(58) Field of Classification Search
CPC .... A61F 5/0127; A61F 5/0113; A61F 5/0111; A61F 2/42; A61F 2/4202; A61F 2/4606; A61F 2/66; A61F 2/6607; A61F 2007/0044; A61F 13/066; A61F 2/60; A61F 2002/6614; A61F 5/0116; A61F 5/0195; A61F 5/14; A61F 13/06; A61F 13/064; A61F 13/045; A61F 2/4225
See application file for complete search history.

(56) References Cited

U.S. PATENT DOCUMENTS

| | | | | |
|---|---|---|---|---|
| 5,741,222 A * | 4/1998 | Fiore | ...... | A61F 5/0106 602/23 |
| 5,853,380 A * | 12/1998 | Miller | ...... | A61F 5/0111 602/27 |
| 6,155,997 A * | 12/2000 | Castro | ...... | A61F 5/0111 602/27 |
| 7,640,680 B1 * | 1/2010 | Castro | ...... | A61F 2/5046 36/140 |
| 7,691,076 B2 * | 4/2010 | Castro | ...... | A61F 5/0127 602/23 |
| 8,048,012 B1 * | 11/2011 | Castro | ...... | A61F 5/0127 602/23 |
| 8,512,269 B1 * | 8/2013 | Stano | ...... | A61F 5/0111 602/27 |
| 9,839,547 B2 * | 12/2017 | Heyd | ...... | A61F 5/0111 |
| 2009/0227927 A1 * | 9/2009 | Frazer | ...... | A61F 5/34 602/27 |
| 2011/0196276 A1 * | 8/2011 | Kuhn | ...... | A61F 5/0127 602/27 |
| 2013/0102940 A1 * | 4/2013 | Joseph | ...... | A61F 5/0111 602/7 |

* cited by examiner

*Primary Examiner* — Tarla R Patel
(74) *Attorney, Agent, or Firm* — DiMarino, Lehrer & Collazo, P.C.; Emmett S. Collazo, Esquire

(57) ABSTRACT

The present invention relates to medical devices and more particularly to medical devices for joint, bone, and tissue support. A brace system is disclosed incorporating at least two shells placed around an ankle and foot area, with straps and laces. The inner boot incorporates a lace-up removable, molded inner boot. The outer boot includes straps for securing the outer boot to the inner boot and for providing targeted support areas for orthotic purposes.

21 Claims, 4 Drawing Sheets

ORTHOTICS BRACE AND SYSTEM

BACKGROUND OF THE INVENTION

The specialty of orthotics focuses on the design and application of externally applied devices used to modify or maintain structural and functional characteristics of the neuromuscular and skeletal system. An orthosis may be used to control guide, or immobilize extremities, joints, or body segments, assist in movement, reduce weight bearing force, aid rehabilitation, correct shape or function, reduce pain, aid performance, or other uses.

In the field of lower-limb orthoses, external devices are applied to lower-body segments to, for example, control motion, provide support, stabilize, reduce pain through transferring load to another area, correct flexible deformities, and preventing progression of deformities. Frequently, orthoses are used for foot or ankle conditions or for aid.

Foot orthotics are devices inserted into shoes, around shoes, as a replacement of shoes, or the like, to provide support for the foot by redistributing ground reaction forces acting on the foot joints while standing, walking, running, or while immobile. They may be either pre-molded or prefabricated or customized with an impression of the foot. Orthotics may impact not just foot or knee problems, but also hip, spine, and other medical conditions. Proper use may aid athletes, the elderly, or others for skeletal or, for example, soft tissue conditions. Custom-made foot orthoses are effective at reducing pain for people with, for example, painful high-arched feet, fractures or breaks, and may be effective for people with rheumatoid arthritis, plantar fasciitis or hallux valgus (commonly called bunions), and many other conditions. For children with juvenile idiopathic arthritis (JIA), custom-made and prefabricated foot orthoses may also reduce foot pain. Foot orthoses may also be used in conjunction with properly fitted orthopedic footwear in the prevention of foot ulcers in the at-risk diabetic foot patient.

Orthotics may also be used for ulcer healing purposes. A custom-made ankle/foot orthosis for the treatment of patients having plantar ulcers is disclosed may incorporate elements of a rigid. L-shaped support member and a rigid anterior support shell hingedly articulated to the L-shaped support member. The plantar portion of the L-shaped member may further comprise at least one ulcer-protecting hollow spatially located for fitted placement in inferior adjacency to a user's plantar ulcer, thus allowing the user to transfer the user's weight away from the plantar ulcer and facilitating plantar ulcer treatment. The anterior support shell is designed for lateral hinged attachment to the L-shaped member to take advantage of medial tibial flare structure for enhancing; the weight-bearing properties of the disclosed orthosis. A flexible, polyethylene hinge member hingedly attaches the anterior support shell to the L-shaped member and securing straps securely attach the anterior support shell in fixed, weight-bearing relation about the proximal, anterior portion of the user's lower leg.

Prophylactic braces are used primarily by athletes participating in contact sports. Evidence about prophylactic knee braces, the ones football linemen wear that are often rigid with a knee hinge, indicates they are ineffective in reducing anterior cruciate ligament tears, but may be helpful in resisting medial and lateral collateral ligament, tears.

Functional braces are designed for use by people who have already experienced a knee injury and need support to recover from it. They are also indicated to help people who are suffering from pain associated with arthritis. They are intended to reduce the rotation of the knee and support stability, They reduce the chance of hyperextension and increase the agility and strength of the knee. The majority of these are made of elastic. They are the least expensive of all braces and are easily found in a variety of sizes.

Rehabilitation braces are used to limit the movement of the knee in both medial and lateral directions—these braces often have an adjustable range of motion stop potential for limiting flexion and extension following ACL reconstruction. They are primarily used after injury or surgery to immobilize the leg. They are larger in size than other braces, due to their function.

An ankle-foot orthosis (AFO) is an orthosis or brace that encumbers the ankle and foot. AFOs are externally applied and intended to control position and motion of the ankle, compensate for weakness, or correct deformities. AFOs can be used to support weak limbs, or to position a limb with contracted muscles into a more normal position. They are also used to immobilize the ankle and lower leg in the presence of arthritis or fracture, and to correct foot drop; an AFO may also be called a foot-drop brace. The base cost of an AFO is often expensive due to numerous factors, both due to manufacturing costs and due to changing patient characteristics. An AFO is generally constructed of lightweight polypropylene-based plastic with the upright portion behind the calf and the lower portion running under the foot.

Obtaining a good fit with an AFO typically involves two approaches. First, professionals may use an off-the-shelf or prefabricated AFO matched in size to the end user. Second, professionals may make a custom manufacture of an individualized AFO from a positive model, obtained from a negative cast or the use of computer-aided imaging, design, and milling. Plastics used to create a durable AFO must typically be heated to high temperatures, making direct molding of the material on the end user impossible.

Four major types of AFOs are flexible AFOs, anti-talus AFOs, rigid AFOs, and Tamarack Flexure Joint AFOs.

To stop or limit or assist knee or ankle motion, a knee-ankle-foot orthosis (KAFO) may function in one or all the three planes of motion in a human joint: sagittal, coronal, and axial. Mechanical hinges, as well as electrically controlled hinges have been used. Various materials for fabrication of a KAFO include but are not limited to metals, plastics, fabrics, and leather. Conditions that might benefit from the use of a KAM include paralysis, joint laxity or arthritis, fracture, and others. Although not as widely used as knee orthoses, KAFOs can make a real difference in the life of a paralyzed person, helping them to walk. These devices are expensive and require maintenance.

SUMMARY OF THE INVENTION

The present invention relates to the fabrication of orthotic devices, for example devices for securing to a patient's foot or leg. Such devices may be used to maintain constant pressure against the foot, sole and ankle of the patient for therapeutic purposes, but also for arm, wrist, torso, or other purposes, to include purposes both therapeutic and athletic.

Some prior art devices of provide for leg, ankle and foot stabilization using assemblies interconnected by hinges of an elastomeric material or two or more shells affixed to one another to form a single brace in what is commonly referred to in the industry as an "Arizona brace." An Arizona brace generally contains a plastic shell made of polypropylene, and leather boot affixed thereto. The Arizona Brace is prescribed to stabilize the ankle, talocalcaneal, midtarsal and subtalar joints. Inside a plastic shell, such a brace has a glued plastizote layer, which is a soft foam, and affixed to that, a mold of a patient's foot, and to that, additional glued layer of leather. An outer leather layer often exists, as well, with the entire product creating one solid unit.

In embodiments of the present invention, an unbroken "L" shape composed of at least two shells provides flexibility of use in combination with rigidity, while other designs (with a jointed ankle) provide different types of control. No leather is required for any shell, nor is it desired for comfort or medical purposes.

Instead of leather, embodiments of the invention include an orthotic foot brace having an at least two leg or foot components, non-adjustable in fit but adjustable in rigidity of hook and loop fastener tautness and lacing, and straps for security, support, and also options for patient compliance, cleanability, and wearability in multiple practical situations.

Embodiments of the instant invention include two separate and separable brace components for use by patients. The molding of an inner brace prevents adjustments, defects, or wrinkles. Use of non-fabric materials to create the brace further reduces the risk of discomfort and health problems related to wear of a fabric-based product. The mold allows for setting any angular inclination in the mold. Fabric foot and leg engagement straps may be used to attach the two separate components of the mold to one another. A securing apparatus allows for limited plantar flexion and dorsiflexion of the foot portion of the sagittal plane by the hinge assembly that can be locked at any point within the sagittal plane range of movement.

DETAILED DESCRIPTION OF THE INVENTION

An embodiment of the present invention is directed to an ankle-foot orthotic for applying a secure, two-shell support system to allow a wearer to conduct activities, to adapt to multiple scenarios at home, at work, or in more taxing physical situations, while promoting patient wear compliance through wearability, cleanability, and comfort features.

An ankle-foot orthotic embodiment of this invention for treating multiple medical conditions or deformities generally comprises at least two shells forming an ankle and lower-leg brace, one shell being inserted into the other. Embodiments feature highly customizable fittings for each shell due to molding properties of insert fabrication materials. Duraflex molding material or a similar product is usually heated to approximately 325 degrees for two minutes before it becomes malleable to shape around the relevant portion of the patient's anatomy. The mold may be placed in the oven for approximately two minutes, removed while hot with welding or similar gloves, draped over a positive mold of a leg, then vacuumed to the positive mold of leg, then 7-10 min harden, then cuts are made. This creates embodiments for a molded inner boot part.

The outer shell of embodiments is comprised of copolymer or polypropylene or other similar type of plastic, heated to approximately 400 degrees Fahrenheit until sufficiently hot, draped over positive patient mold, let sit for 1 hour to mature, then after an hour the mold is cut and modified. The outer mold is then placed over the positive Both materials are approximately ⅛ inch thick. Both are truly custom molded to the patient's anatomy. The copolymer may be a mix of polypropylene and ethylene, where the copolymer is frequently harder than polypropylene. Embodiments may create the outer shell by way of heating the shell at 400 degrees F. for 3 min to 5 min, depending on the mix of plastic, making it harder or softer.

Embodiments may include an at least one mid- to high-ankle strap for horizontal circumferential security of the outer shell around the inner shell, for support, for stabilization, and for other features. Embodiments may also include an at least one second strap that follows below the foot arch, across the midfoot to anterior ankle area, and secures circumferentially at a horizontal plane above the lateral to medial ankle area.

Figure 1:
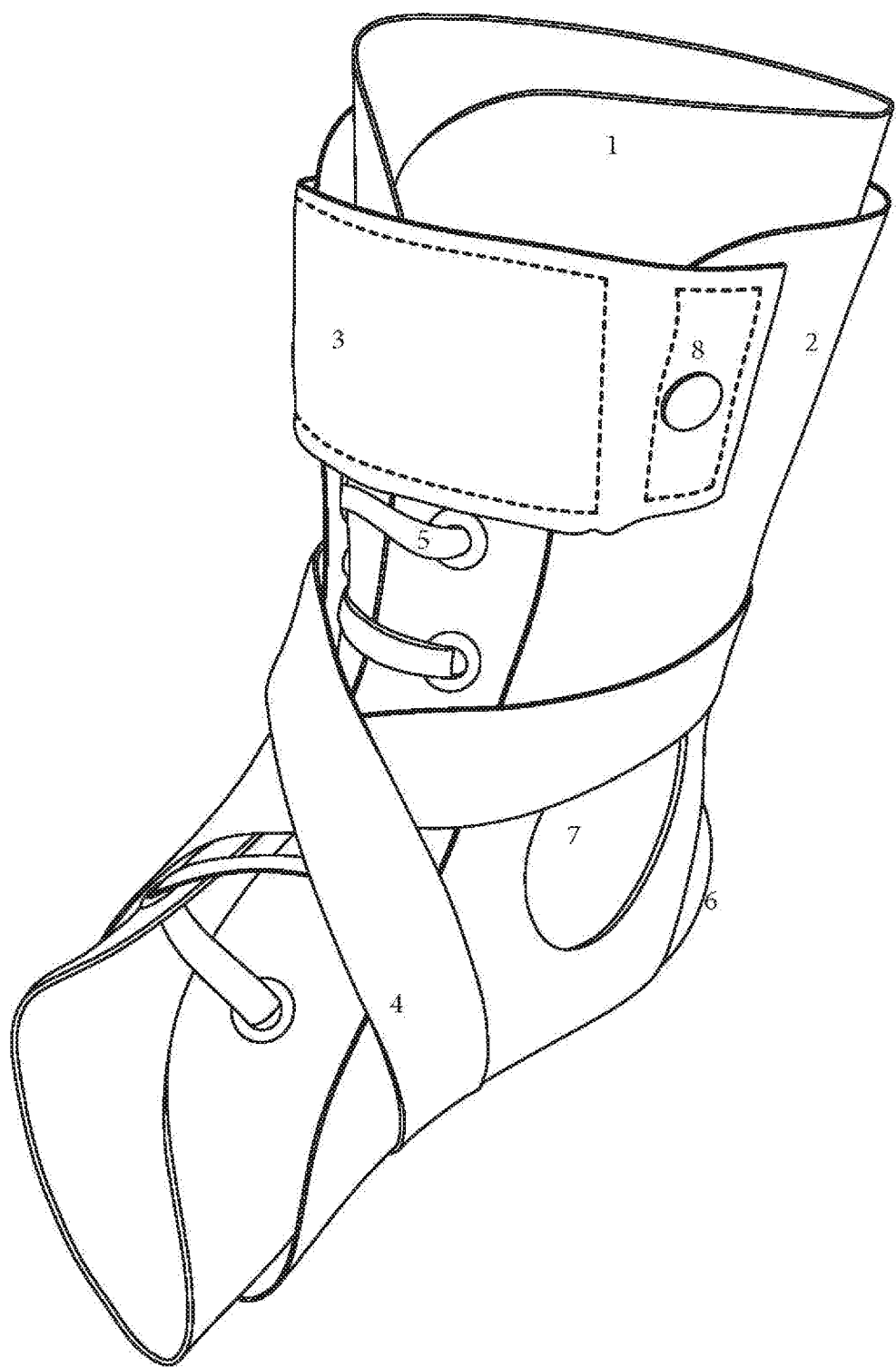
FIG. 1 is a front perspective view of an embodiment wherein the embodiment is strapped and laced.

An embodiment of the invention will now be described. As shown in FIG. 1, an inner immobilizing shell 1 is located within an outer immobilizing shell. An ankle support strap 3 may be affixed to one side of the upper ankle area of the outer shell, for example with a button, snap, rivet 8, for withstanding high tension as on a medical immobilizing garment. A second cross strap is affixed to the outer shell and is used to wind about the outer shell to provide comfort and medically enough support about the necessary areas. For example, in FIG. 1, the second strap 4 proceeds from the midfoot or mid-ankle area to the posterior of the ankle in a horizontal plane, continues to the opposite side of the same plane, to an area across the gap in the outer shell, and then the second strap proceeds across the area approximately between the lower midfoot and Lisfranc's Joint areas, underneath the middle of the sole to provide support to the lateral plantar, medial planter, and saphenous areas, with some added support to the tibial and sural areas. The strap then proceeds back across the area between the midfoot and Lisfranc's Joint areas and affixes, for example with hook and loop fasteners, at approximately the area where the strap began. Embodiments of the invention will have medial ankle 7 and heel sections removed for the less rigid inner boot component to flex in those areas. The top strap 3 functions to hold the exterior frame onto the interior frame.

In embodiments, the outer shell will be comprised of cleanable plastic material, where soap and water may remove any debris, dirt, sweat, or other human or clothing waste, odor, smells.

Figure 2A:
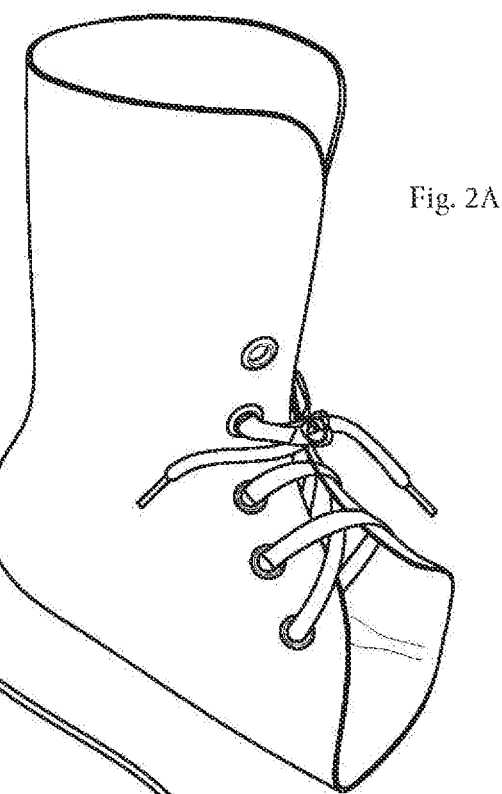
FIG. 2A is a perspective view of an embodiment of an inner shell that fits inside of the outer shell in FIG. 2B.
Figure 2B:
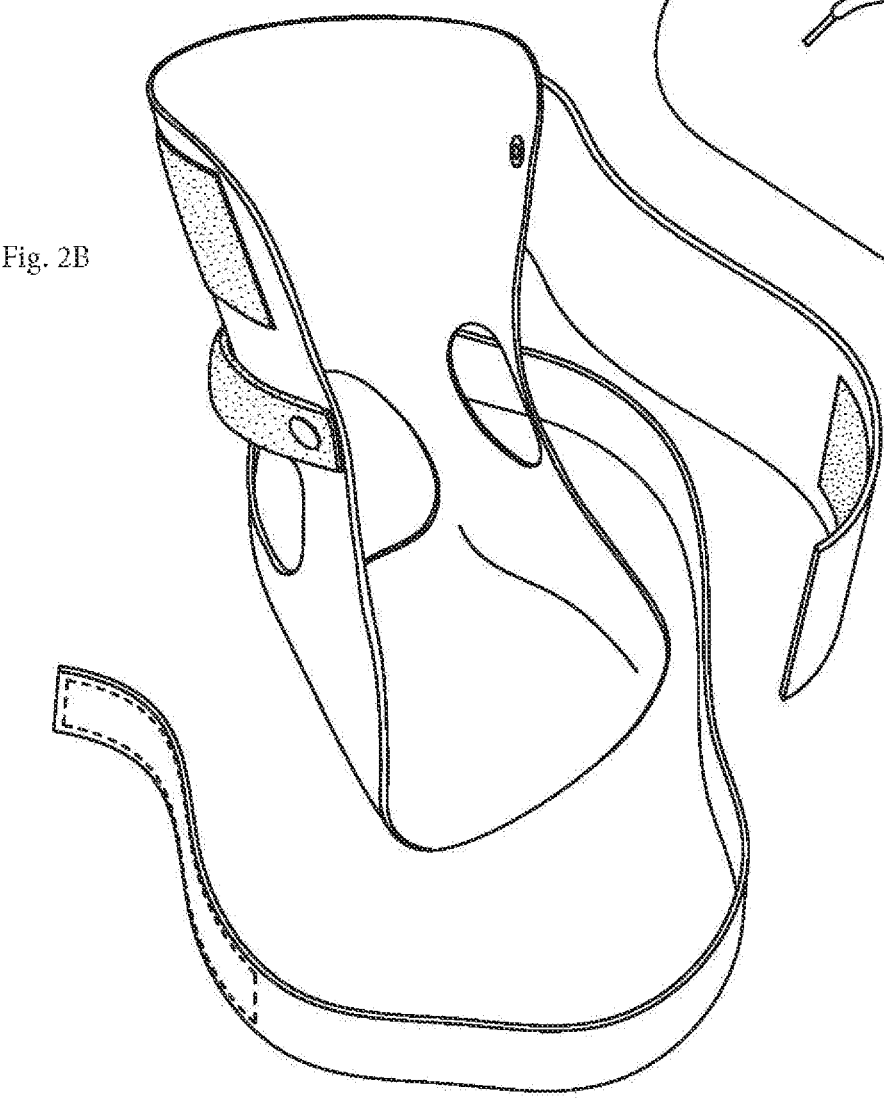
FIG. 2B is a perspective view of an embodiment of an outer shell that receives the inner shell in FIG. 2A.
Figure 3:
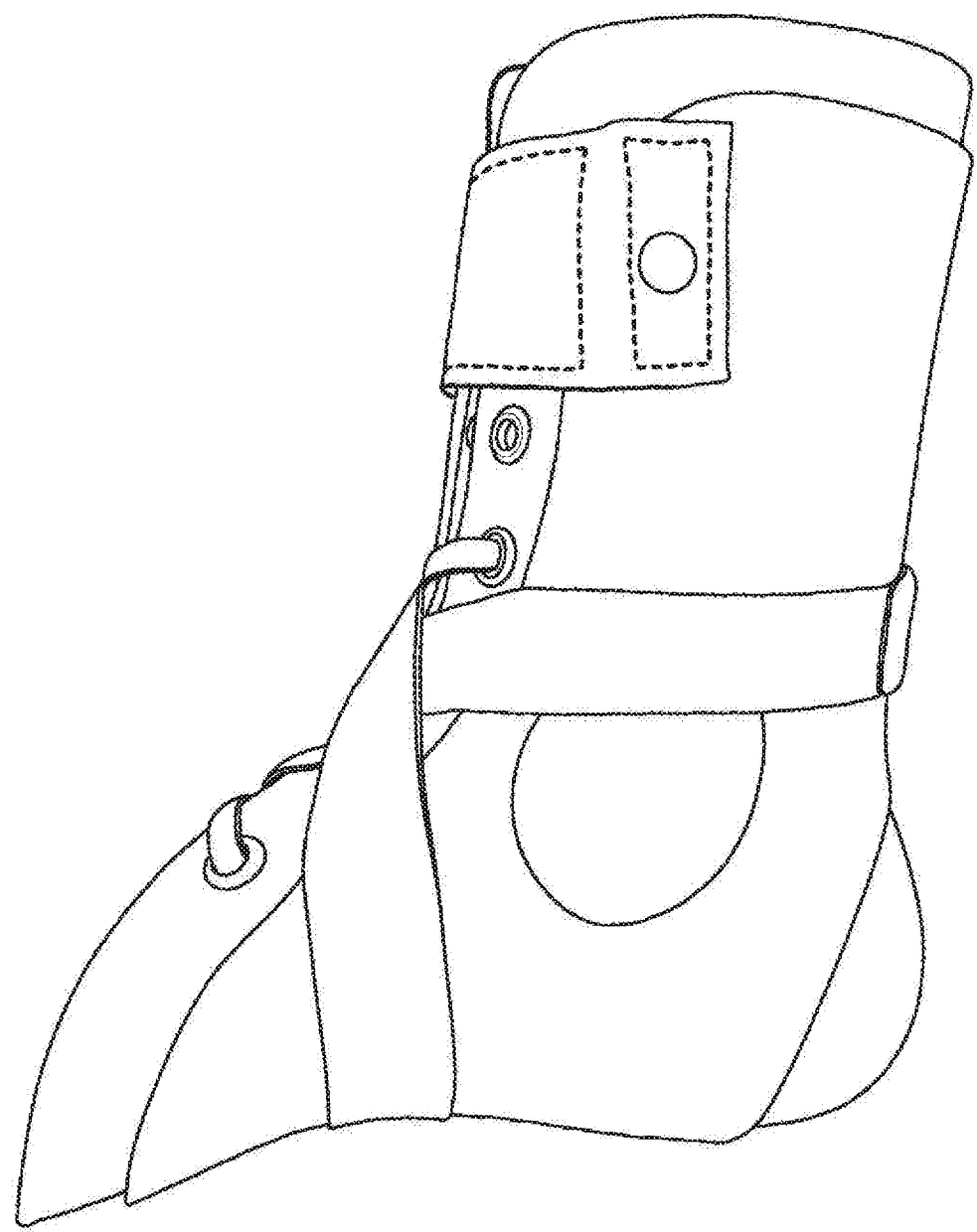
FIG. 3 is a side view of an embodiment of the invention wherein the inner shell is secured within the outer shell which is also secured.

Optionally, and for temporary, minimal activity evolutions, a patient or wearer may only use the inner boot, for example for at home, nearly sedentary activity. The outer shell (FIG. 2B) may be then used for outdoor activity of whatever kind applicable. The unit, together, may be of such a fit as to be supportive and secure for medical purposes, but also, due to the materials, the fit, and the compact nature, able to fit into a wearer's normal as to be able to be worn in footwear typical for the patient.

Alternative embodiments of the invention include but are not limited to use of more than two shells, a high-ankle or higher orthotic, a low-ankle or lower orthotic, wrist, upper body, lower body, knees, ankles, or, hips, for example, where a mold would be used of the trunk of the body. For example, for a custom mold for the wrist, the cast mold of the positive would be created, the above descriptions applicable to the pour, modifying processes, placing Duraflex or similar materials in an applicable heating system or oven, making an inner liner, placing the copolymer in a heating system or oven, providing a molded product for a patient's use. The result is a waterproof, removeable, cleanable product, with replacement parts available. The resulting product can be used to safeguard, secure, brace, and/or aid in the healing of problems including the spinal, back, sprains, strains, ligament or tendon concerns, all fractures, and other roles.

Still additional benefits exist. For example, benefits over the more standard and commonly used Arizona brace are that the instant invention does not result in stretches of the unit, which can create problems for older patents, for example with diabetic patients, which can develop into units that have wrinkles. If, for example, a wrinkle, tear, ripple, or other deformity in the leather impacts a diabetic ulcer, there is a possibility of not only further irritation that could preclude use of the orthotic brace, but even loss of a leg. This is a distinguishing feature from embodiments of the instant invention, which does not create opportunities as with leather for wrinkles or other deformities. Embodiments of this invention promote total contact between the orthotic and the patient. Embodiments of the instant invention minimize risk of slippage or of migration.

As an example of a current used brace, the industry's Arizona brace is frequently comprised of a plastic shell, typically polypropylene, and inside the plastic shell a soft foam material is glued, and over the soft foam material is glued leather, forming one solid unit. Embodiments of the invention, due to not only support but total contact and true circumferential support, may be used for medial lateral support, planter dorsi support, circumferential compression support and other support requirements for many conditions, including but not limited to consequences of posterior tibial tendon dysfunction, talocalcaneal varus or valgus, charcot foot, severe pronation of planus, chronic achilles tendonitis, tibialis tendonitis (posterior or anterior), ankle arthritis or degenerative joint disease, ankle, suntalar, midtarsal trauma, drop foot, certain symptoms of certain forms of cancer, chronic ankle instability, post fracture of the distal tibia or fibula, post fractures of the distal tibia or fibula, post fractures of the ankle, subtalar and midtarsal trauma, osteoarthritis of the ankle and/or foot, and other conditions.

In addition to properties of flex and cleanability, embodiments of the orthotic brace system may employ a Duraflex or similar material which may incorporate properties of forming a mold that provides total or near total contact to the patient's anatomy, or likewise emphasizing a comfortable supporting mold that takes shape of each individual's anatomy while being flexible and soft to not cause abrasion, soreness (due to flexibility), and allowing the firmer copolymer outer shell to provide the requisite support and rigidity that would otherwise create abrasion, soreness, redness, irritation, etc., of patient's anatomy.

Figure 4:
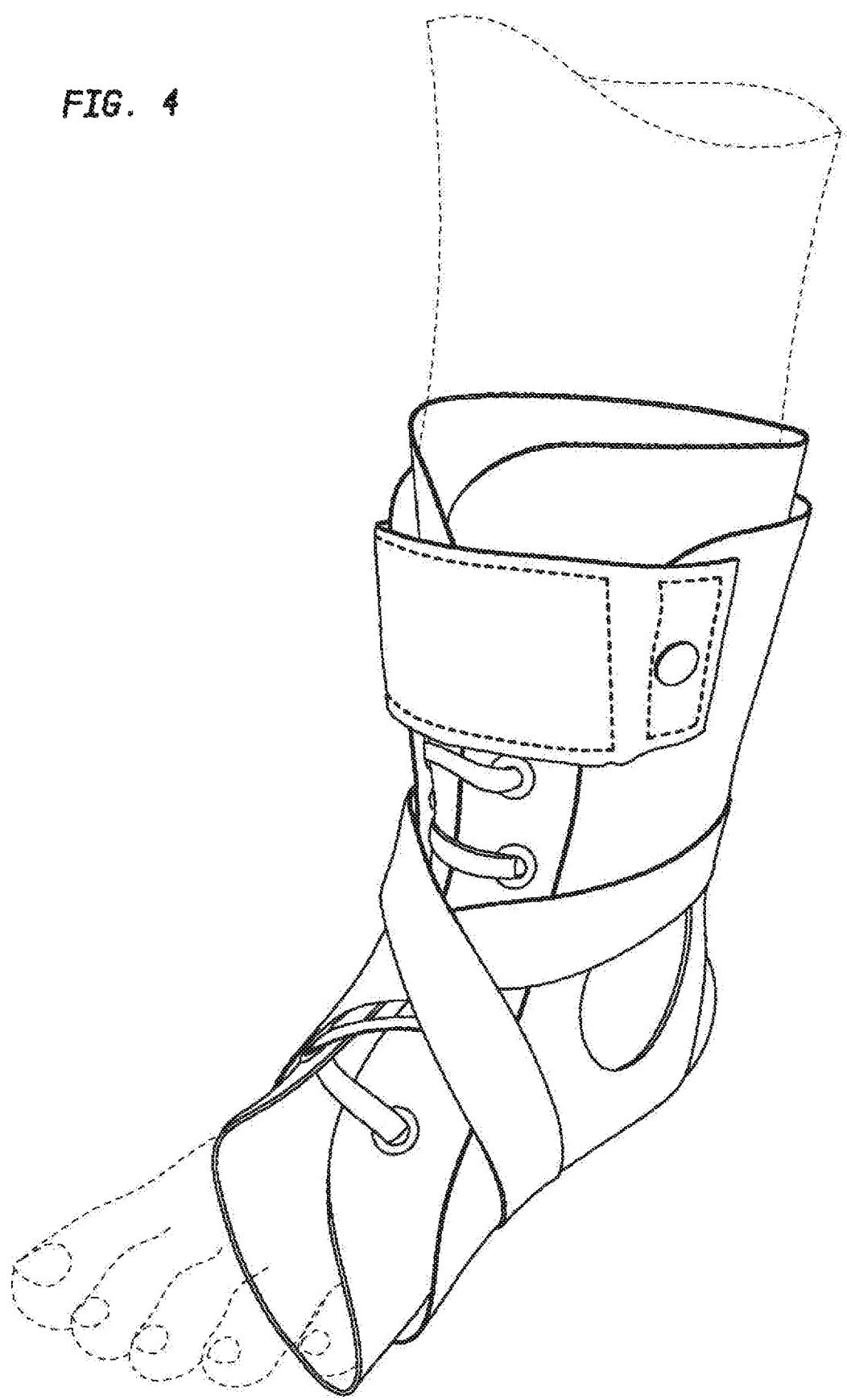
FIG. 4 is a perspective view of an embodiment of the invention, where the embodiment is created to reach a mid-ankle height, secured as a KAFO.

According to an embodiment of the present invention, the elastic strap may be the outer shell to be wrapped in a crossing loop taking the approximate shape represented in FIGS. 1 and 4, where the second strap crosses the midfoot or Lisfranc's Joint area, proceeding around the medial, middle, and lateral arches, and back to the mid- to low-ankle area. In embodiments, the strap is angled at several ideal angles to provide the correct tension force for maintaining security of the brace and the support and rigidity to the outer shell and thereby to the patient.

Additional modifications to embodiments of the brace system may be cost-effectively made, despite major changes to patient biology characteristics. For example, if a modification is needed due to a medical condition, the straps may be removed, shells may be removed, and the outer or inner shell may be modified. An example would be to optionally cut out the lateral and medial malleoli from the outer shell, the malleolus ankle bone, or the heel. See FIG. 1. The outer shell can be custom modified to all patient's concerns regarding pressure, soreness, incision cites, ulceration, etc. Therefore, other embodiments are available, to include trimming edges to reduce contact areas as needed. To the extent additional modification is required, for example due to weight loss or other conditions or developments, the plastics of the outer shell is heat moldable, which is not an available modification option with the Arizona brace.

Concerning hygiene, a typical Arizona brace may take on odor. It may get dirty through normal daily use, and cleanliness is a difficulty that impacts wearability and patient compliance. Embodiments of the instant invention are comprised of hypoallergenic materials, so soapy water applications or similarly accessible options may be used to wipe away odors or other conditions and restore the brace system for clean use. Due to the brace being waterproof (except for option of laces which may hold water) the patient may use embodiments of the brace system in the shower, the pool, or during aqua therapy, travelling to the beach, or any other circumstance where water may be applicable. New, dry laces are an option for the system to ensure the system is as waterproof and dry as possible.

Optionally, wearers may apply the device without the rigid shell where consistent, 100% support is not required, but only 60% to 70% for relevant low-stress activities. As an example, this inner shell may be worn inside a bedroom slipper or house footwear to allow for increased patient compliance over and above industry standard products, such as an Arizona brace which many patients find to be too bulky, potentially odorous after a period of time, and which may not fit into house footwear due to bulk.

Regarding potential problems with a patient's navicular bone (medial side of foot, for collapsed midfoot, pronation, etc.), for example a prominent navicular bone or other areas of discomfort, the shells may be modified accordingly. If the navicular bone is prominent, the brace may be modified by taking the relevant area of the brace's outer shell and cutting it out, as with cutting out the medial lateral ankle as shown in FIG. 1 Similar options exist where patients need pressure area relief, such as incisions being required due to prior or recent surgeries, arch collapse, and other conditions, deformities, and temporary or long-lasting ailments, complaints, or other medical- or athletic-related concerns.

Regarding long-lasting conditions, other custom molded products, such as AFOs or other casts, may eventually lead to atrophy. The cast becomes too big large, potentially lacking the support and brace system that the patient's anatomy required. The patient's anatomy may slide in a typical brace system, such as an Arizona brace, or swelling may lead to inaccurate fits in such products. With embodiments of the instant invention, however, if atrophying occurs after, for example, six to eight weeks of use, the user may tighten up the laces, or a modest five- to fifteen minute adjustment modification may occur to allow for a more custom fit for the swelling or atrophying, reducing or eliminating irritation, slippage and migration, and allowing the patient to recover proper support.

In embodiments, the securing or fastening of the boot is not the sole means of supplying support. Fastening the straps, which in embodiments may follow different patterns, provide specific, consistent support, for example for posterior tibial tendon disfunction PTTD. In most embodiments, whether for foot or ankle or other parts of the body, benefits are often due to characteristics of being form fitting, providing total contact, providing a comfortable snug fit, reducing or eliminating slippage, and resulting in total immobilization. Further, depending on the specific user's needs, Embodiments may also incorporate an above-ankle strap, to support and control ankle instabilities, and prevent slippage or migration and anterior rotating.

While this may apply for PTTD, the brace system provides for solutions to Achilles tendonitis, Achilles bursitis, Achilles tears, nondisplaced fractures, and other conditions noted above, plus additional conditions or therapeutic scenarios, to include athletic support. The invention is not limited to embodiments that support and control hindfoot and midfoot, nor even limited to support for anti-pronation, and arch for uplift at the relevant tendon and bony structure areas alone.

In addition to providing advantages over typically braces that provide a rigid plastic with foam liner that results in an abrasive, non-moldable, non-malleable liner, embodiments of the instant invention also solve an issue that some patients have with negative pressure. Negative pressure is a problem where, for example for a wrist styloid bone, with prominent styloid, we can modify device to not have any negative pressure due to cutouts. This may be equally applicable for a protrusion at the ankle.

Typically, products are sewn or laminated together, leaving very little room for modification after weight loss or weight gain by a patient, or for latent protrusions leading to negative pressure. For embodiments of the invention, if a patient loses, for example, one-half of an inch to an inch in circumference, embodiments can be modified with a scissors, a razor knife tool, to cut down or cut away relevant areas, possibly creating islands of material. Distinguishing from other devices, if one needed to make something smaller down the road for a patient two years, three years, five years due to patient anatomy, weight gain or weight loss, modifications to a new brace provide patients and wearers an order of merit of cost effectiveness, for example what could be modified or made at a minimal cost of approximately $150 is a clearly better choice for most wearers and patients than a new brace at $1,800.

Embodiments of the invention may have with a thickness of outer 1 and inner 2 shells, together, of approximately 4 to 4.5 mm or less at the mid-ankle or lower-ankle area. However, for different purposes, the thickness may be widened, as will be discussed below.

It is not uncommon for orthotics patients to seek assistance after a period due to an irritation. Embodiments of the instant invention, based in part on materials and based in part on architecture of the system, have reduced risk of irritation. See above discussion of leather, ripples, and tears. However, if an irritation does arise, typically because of a patient or wearer's anatomical change, a modification may be made to the brace system. Unlike re-upholstering bulky leather components, where the leather wears away, It is not uncommon for patients to ask if a leather-molded product can be "patched" like clothing. This is not provided because a patch can wear away, tear, ripple, or develop an inconsistency that creates further problems for the patient.

It is not cost-effective for the patient to make multiple modifications and adjustments or repairs with an Arizona brace. The instant invention overcomes this issue for the reasons given and those apparent to those having ordinary skill in the art. Typically, the way other orthotics are cleaned is with leather cleaner or shoe polish, which do not result in the relatively odorless and cleaner product as with cleaning embodiments of the instant invention with soapy water, not to mention the ability to thoroughly dry the instant embodiments.

The only thing that would have to replace, for example after 18 months or 24 months, is a strap or new laces, which carry minimal cost compared to the cost of embodiments of the invention. Notably, embodiments may incorporate hook and loop fasteners instead of laces (see FIG. 1). For example, for some patients, such as arthritic patients or diabetics, hook and loop fasteners are preferred, and this element increases compliance and therefore overall health. The same remedy of hook and loop fasteners instead of laces may also apply with patients who are obese, have back or other problems, and where securing with overlapping straps best allows for patient compliance. For still other embodiments, for example a wrist embodiment, a preferred embodiment may be one where an inner, removeable flex shell exists and where only the outer shell has the strapping, whether laces or hook and loop fasteners.

Further, the soft flexible dorsiflex material of the inner shell not only provides flexibility but also ameliorates what in other objects would become areas of irritation. Additionally, if a given patient within, for example, six to eight months has another surgery or if a medical condition worsens, embodiments of the instant invention are modifiable. Orthotics professionals can take the inner or the outer portion of the device and modify the module to conform to that patient's new requirements, which may be related to injury, weight loss, weight gain, or other concerns or issues. There may be no need to re-form a mold or module component or even make a new cast. In some circumstances, the orthotics professional can cut away portions of the old modules or moldings.

To fabricate embodiments, a drill press may be used to secure hook and loop fastener straps to shell(s) of a brace, for example using stainless steel rivets. Sanding cones may be applied in three different forms. One is coarse, one is non-coarse, one is for finishing. The outer shell receives the coarse sanding cone to modify and shape the trimlines to custom fit the positive mold. Next, the finer cone is used smooth the shell along the edges. Then a finishing cone is used on all the edges to eliminate irritation against the skin. A drill press may be used to provide eyelets (e.g., brass) for laces. Brass may be used so the eyelets do not rust.

For modifications with common braces used today, an orthotics professional would need to remake the brace, requiring removing both the inner and outer layers of leather, and then remolding the structure, if such a redo can be done. This requires tearing down the entire brace and essentially starting over, and later redoing the leather. Instead of such obstacles, which combine to prevent patient compliance, combinations of characteristics of embodiments of this invention incentivize use of the system by the patient, such as due to wash-ability, cleanability, form-holding and lasting comfort fit, odor-lessness, support strap placement, or other characteristics.

Additional options for embodiments of the invention include but are not limited to a height brace for posterior tibial tendinitis dysfunction or for collapse of mid foot forming a flat foot, which provides benefits where bones and arteries start to deteriorate. A higher brace will suffice to support those conditions from the ankle down. With a patient who had a stroke, or drop foot, skiing fracture of tibia or fibula, for example just above the ankle, then the brace may be made approximately 16-18 inches high, for a typical patient. The required height may be higher or lower and will result in the brace capturing and supporting the tibia or fibula and the higher the brace extends, the more leverage at the foot.

If a patient has drop foot from back injury, stroke, nerve injury, and creates drop foot, embodiment will likely be created by casting a patient's mold at an approximately 90-degree angle, so that every step the patient takes is automatically heel strike. Alternatively, for some conditions, such as a fractured heel, the mold may be formed so that the no heel strike is automatic. Embodiments may incorporate modifications of the mold after taking patient cast to customize in a swing phase to allow for the strike at the midfoot, never putting pressure on the heel.

For purposes of clarity, drop foot and other relevant conditions may result from spinal cord injury or other accident, or stroke; drop foot is the condition where no control of dorsiflexion, or lifting foot or toes. Other embodiments may aid patients dealing with dragging toe, which could lead to a trip, a fall on shoulder, face, etc., and other predetermined configurations. For example, if embodiments are made for drop foot only nine inches above the floor the 4.9 inches with a foot wanting to plant, the top edge of this brace may cut into the lane and then we come over the gash rocks that an inch below the fibula head. The result is extra leverage to hold the foot up more in a dorsiflex position. Alternative embodiments may incorporate a thin plastic, such as a polypropylene polyethylene, which is not a dorsiflex material. With such modifications, the brace aids patient compliance by producing the product at a faster rate, in addition to the other factors, such as comfort, flexibility, ease of wear, open front with lacing, ease of cleaning, modifiability of the brace if the patient loses circumference, etc.

Regarding use of the brace for athletic support, the brace may incorporate an outer shell of larger width, for example 5/32 inches, 3/16 inches, 1/4 inches, 3/8 inches, or 1/2 inches. For example, for a professional contact sport, an athlete with a stressed or strained Achilles tendon can employ a brace that limits dorsiflexion and planar flexion of foot, which limits extension of Achilles tendon during activities. Alternatively, if the forearm is a location of a condition, for example at the radius and ulna, where one is fractured and a cast is not preferable, a brace system may be used instead.

Having described and illustrated the principles of the invention through the descriptions of various embodiments thereof, it will be readily apparent to those skilled in the art that the invention can be modified in arrangement and detail without departing from such principles. The claims should be interpreted to cover all such variations and modifications.

I claim:

1. A system to form a custom therapeutic brace for use on a patient comprised of:
   an inner cast member, where the inner cast allows for selected areas of the inner cast to accommodate anatomical protrusions or requirements associated with a patient's anatomy,
   where the inner cast member is molded and laced, and replicates properties of an at least one portion of the patient's anatomy,
   an outer cast member, where the outer cast member is comprised of attachment points on said outer cast member, and where the outer cast member contains an at least one hook and loop fastener strap for securing the outer cast member around the inner cast member, and
   where the inner cast member is comprised of a fiberglass reinforced plastic material that is heated at approximately 325 degrees for two minutes, removing the material while hot, draping the material on a positive mold of a patient's anatomy, vacuuming, the material to the positive mold, hardening for approximately seven to ten minutes, and applying any required incisions.

2. The system of claim 1 where the outer cast member contains two bands of hook and loop fastening to secure the outer cast member around the inner cast member and provides support to the patient.

3. The system of claim 2 where an outer shell further comprises an at least one cut away for allowing protrusions and for reducing a risk of negative pressure, and for allowing an inner shell to at least partially protrude through the outer shell.

4. The system of claim 1 where the inner cast member contains a fastener to secure the inner cast member, the fastener selected from the group of an at least one hook and loop fastener, an at least one zipper, an at least one button snap, magnets, and laces.

5. The system of claim 1 where an outer cast member is comprised of a material selected from the group of copolymer, polypropylene, polypropylene and ethylene, and plastic resin, the member s heated at approximately 400 degrees Fahrenheit, the member s draped over a positive patient mold and allowed to sit for approximately one hour to mature, and applying cuts and modifications to the outer cast member.

6. The system of claim 5 where the heating lasts for between three and five minutes for a predetermined amount of hardness or softness.

7. The system of claim 1 where the at least one hook and loop fastener strap is a mid- to high-ankle strap for horizontal circumferential security of an outer shell around an inner shell.

8. The system of claim 7 further comprising an at least one second strap that follows below the foot arch, across the midfoot to anterior ankle area, and secures circumferentially at a horizontal plane above the lateral to medial ankle area.

9. The system of claim 1, where a system's inner and outer members are made of a thermoplastic material formed in part by applying a vacuum to said heated thermoplastic material to pull said thermoplastic material tightly about the inner and outer member stocking material,
   cooling a resulting vacuumed formed thermoplastic material, and
   cutting away a custom leg portion and a custom foot portion.

10. The system creating an orthotic brace of claim 1, where the brace is used for athletic support, and the brace comprises an outer shell of width selected from the group of 5/32 inches, 3/16 inches, 1/4 inches, 3/8 inches, and 1/2 inches, and where the brace limits dorsiflexion and planar flexion.

11. The orthotic brace of claim 1, where an outer shell is further comprised of a fastener selected from the group of hook and loop fasteners, laces, buttons, an at least one zipper, or an at least one button snap.

12. The orthotic brace of claim 1, where an at least one strap is comprised of a first ankle support strap that is affixed to one side of an upper ankle area of an outer shell member for withstanding high tension, and a second strap that is affixed to the outer shell member that winds about the outer shell member from a patient's midfoot and mid-ankle area to a posterior of a patient's ankle in a horizontal plane, continues to an opposite side of the same plane, to an area across a gap in the outer shell, and then the second strap proceeds across an area approximately between the lower midfoot and Lisfranc's Joint areas of the patient's anatomy, underneath a middle of a sole to provide support to the lateral plantar, medial planter, and saphenous areas, with added support to the tibial and sural areas, and then proceeds back across the area between the midfoot and Lisfranc's Joint areas and affixes at approximately the area where the strap began.

13. The orthotic brace of claim 12, further comprising removal of medial ankle and heel sections.

14. The orthotic brace of claim 1, further comprising stainless steel rivets for affixing an at least one strap, eyelets, and laces.

15. The orthotic brace of claim 1, where the orthotic brace is a foot and ankle orthotic, and where a patient's mold is fabricated at an approximately 90-degree angle.

16. The orthotic brace of claim 1, where the orthotic brace is a foot and ankle orthotic, and where the mold is customized for a swing phase to result in a strike at the midfoot.

17. An orthotic brace comprised of an inner shell that is molded and laced for at least partially surrounding a wearer's foot;
   an outer shell that receives the inner shell;
   at least one mid- to high-ankle strap for horizontal circumferential security of the outer shell around the inner shell;
   an at least one second strap that proceeds below the wearer's foot arch, across a midfoot to anterior ankle area, to secure circumferentially above a lateral to medial ankle area and
   where the inner cast member is comprised of a fiberglass reinforced plastic material that is heated at approximately 325 degrees for two minutes, removing the material while hot, draping the material on a positive mold of a patient's anatomy, vacuuming the material to the positive mold, hardening for approximately seven to ten minutes, and applying any required incisions.

18. The orthotic brace of claim 17 where the inner shell is further comprised of laces for securing the inner shell.

19. The orthotic brace of claim 17 where an at least one section of the outer shell is removed to allow for inner shell to expand through an area selected from a group of medial ankle area, heel, and lateral ankle area.

20. The orthotic brace of claim 17, where the inner shell extends above a patient's knee.

21. The orthotic brace of claim 17, where the inner shell rises to a patient's low ankle area.

\* \* \* \* \*